United States Patent [19]

van Andel

[11] 4,256,719

[45] Mar. 17, 1981

[54] PROCESS FOR THE COMBINED MANUFACTURE OF CHLORINATED HYDROCARBONS AND SODIUM BICARBONATE

[75] Inventor: Eleonoor van Andel, Enschede, Netherlands

[73] Assignee: Akzo N.V., Arnhem, Netherlands

[21] Appl. No.: 110,767

[22] Filed: Jan. 9, 1980

[30] Foreign Application Priority Data

Jan. 10, 1979 [NL] Netherlands .................... 7900183

[51] Int. Cl.³ .............. C01D 7/00; C01D 15/08; C07C 17/02; C07C 17/10
[52] U.S. Cl. ............................. 423/424; 423/429; 423/190; 570/244
[58] Field of Search ............ 423/186, 187, 188, 189, 423/190, 194, 421, 422, 424, 429, 493, 502; 260/654 A, 659 R, 651 A, 660, 662 R, 662 A, 654 R

[56] References Cited

U.S. PATENT DOCUMENTS

| | | | |
|---|---|---|---|
| 1,928,540 | 9/1933 | Lawarree | 423/422 |
| 2,752,222 | 6/1956 | Birman | 423/422 |
| 3,111,379 | 11/1963 | Gancy et al. | 423/424 |
| 3,341,612 | 9/1967 | Hayes et al. | 260/659 A |
| 3,462,501 | 8/1969 | Hörnig et al. | 260/654 A |
| 3,576,893 | 4/1971 | Baird et al. | 260/654 R |
| 3,840,641 | 10/1974 | Wampfler et al. | 423/189 |
| 3,929,964 | 12/1975 | Thoma | 423/555 |
| 3,950,443 | 4/1976 | Prahl | 260/662 A |
| 3,993,586 | 11/1976 | Hagedorn et al. | 260/654 R |
| 4,039,597 | 8/1977 | Tsao | 260/659 R |

FOREIGN PATENT DOCUMENTS

| | | | |
|---|---|---|---|
| 1101683 | 3/1961 | Fed. Rep. of Germany | 423/424 |
| 1403306 | 8/1975 | United Kingdom | 423/424 |

*Primary Examiner*—O. R. Vertiz
*Assistant Examiner*—Gary P. Straub
*Attorney, Agent, or Firm*—Stevens, Davis, Miller & Mosher

[57] ABSTRACT

Production of sodium bicarbonate by the Solvay-soda method, employing a volatile aliphatic amine instead of ammonia, is combined with the oxychlorination of olefins in liquid phase by using the amine hydrochloride side-product of the soda plant as chlorine source in the oxidative regeneration of the spent chlorinating liquid. The chlorinating liquid contains iodine and copper chloride or iron chloride and on regenerating the spent liquid the amine is recovered in the vapor phase and recycled to the soda plant.

5 Claims, 1 Drawing Figure

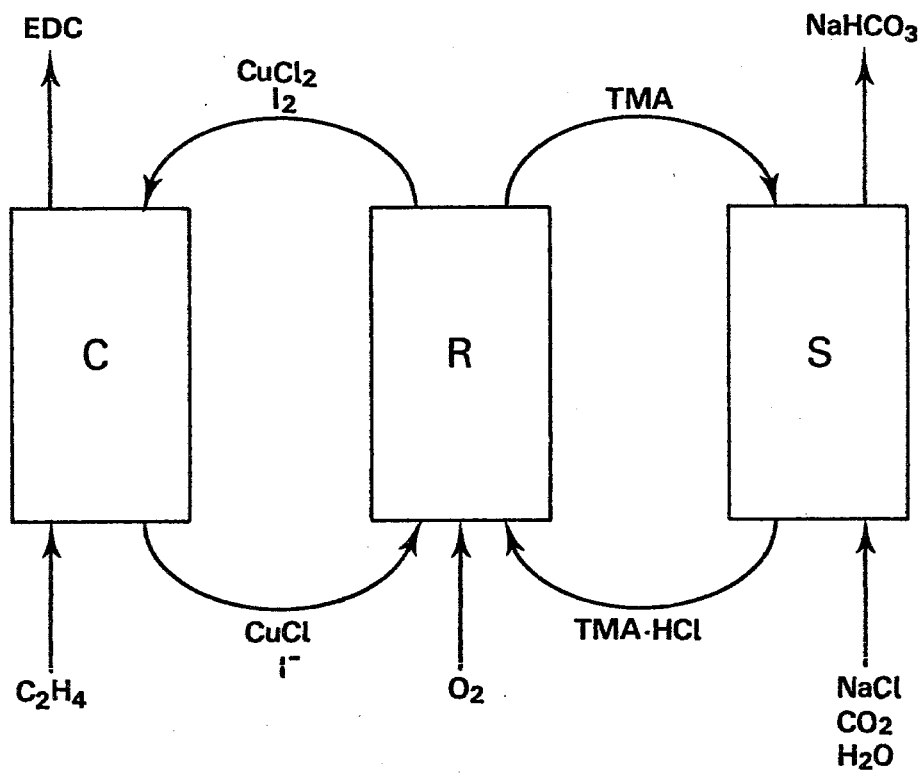

PROCESS FOR THE COMBINED MANUFACTURE OF CHLORINATED HYDROCARBONS AND SODIUM BICARBONATE

The invention is concerned with the combined manufacture of chlorinated hydrocarbons by the chlorination of olefins and sodium bicarbonate by the conversion of common salt according to the Solvaysoda principle. Processes for the separate manufacture of these products are well known in the art. Thus, the technical chlorination of olefins is often carried out with a chloride of a polyvalent metal in the oxidized state as the chlorine transferring agent, using hydrogen chloride as the chlorine source and oxygen for regenerating the metal chloride. This so called oxychlorination process usually employs copper as the polyvalent metal and is widely applied for the manufacture of 1,2-dichloroethane (EDC) from ethylene. EDC is an important starting material for the production of vinylchloride by pyrolysis.

While the oxychlorination reactions are mostly performed in the vapor phase it has been recognized that a liquid phase process has substantial advantages. Thus, in U.S. Pat. No. 3,341,612 it is proposed to use cupric chloride or ferric chloride in a liquid organic nitrile as a liquid phase reaction medium. Of particular interest is the liquid phase process disclosed in U.S. Pat. No. 3,576,893 and as described more particularly in the Journal of Organic Chemistry, pp. 3324–3330 (1971). In this liquid phase process use is made of a substantially non-aquous chlorinating liquid which in addition to copper as the polyvalent metal contains iodine. It is observed that the iodine has a marked catalytic effect on the halogenation with copper (II) chloride.

The technical manufacture of sodium bicarbonate normally follows the Solvay-soda method, wherein sodium chloride is converted by carbonatation into sodium bicarbonate with the aid of ammonia as a recoverable volatile base material. The ammonia is recovered by treating the side-product ammonium chloride with lime and the residual calcium chloride goes to waste. In order to be less wasteful in chloride values it has previously been suggested to employ ammonium chloride formed in the ammonia-soda plant as chlorine source in the oxychlorination of olefins. This suggestion, which can for instance be found in the published Netherlands patent application 7,309,602, is based on the assumption that the ammonia can be recovered and fed back to the soda plant. However, it appears that in the oxychlorination with ammonium chloride as the chlorine source a technically acceptable raction rate is only obtained at about 350° C. and, because of the presence of oxygen, there will then occur oxidation of ammonia to nitrogen and water. In view of the high loss of ammonia this chlorine source is unsuitable for industrial application.

Yet, the possibility of coupling a chlorination process to a Solvay process is of great importance. Not only would it eliminate the calcium chloride waste problem and loss of chloride values associated with the Solvay process, but also the energy wasting electrolysis of common salt to liberate chlorine for chlorinating purposes would not be needed. Thus, for instance a chlorination product like EDC and soda could as it were be directly obtained from ethylene and common salt.

It has now been found that this coupling is very well possible by using a particular chlorinating liquid of the above indicated type and regenerating it with a particular chlorine source that is formed in a soda process of the Solvay type.

Broadly speaking the invention is directed towards the realization of a process for the combined manufacture of chlorinated hydrocarbons and sodium bicarbonate comprising the steps of a. chlorinating an olefinic hydrocarbon with a substantially non-aqueous chlorinating liquid containing iodine and a chloride of a polyvalent metal in the oxidized state, b. converting sodium chloride by carbonatation into sodium bicarbonate with the aid of a volatile base according to the Solvay-soda method, c. using the hydrogen chloride adduct of the volatile base resulting from step b. as the chlorine source in the oxidative regeneration of the spent chlorinating liquid of step a.

According to the invention the process is characterized in that the polyvalent metal in the chlorinating liquid is copper and/or iron, the volatile base in step b. is an aliphatic amine having a boiling point below 100° C. and its hydrochloride adduct is the chlorine source in step c., the amine being recovered in the vapor phase and returned to the soda process of step b.

It has surprisingly been found that such aliphatic amine hydrochloride is an effective chlorine source for the oxidative regeneration of the spent chlorinating liquid. The reaction temperature can be held relatively low, i.e. generally below 200° C., and the amine may be recovered in the vapor form without any appreciable loss. Suitable amines are generally to be found among the various alkyl amines having 1 to 3 carbon atoms in the alkyl group. Specific mention may be made of secondary amines like dimethylamine and diethylamine. Of particular interest are tertiary amines and, considering its volatility and availability, preference goes out to the use of trimethylamine (TMA).

The possibility of using TMA or its homologs as volatile base in the Solvay process instead of ammonia has been known for a long time. See for instance the old Germany patents 5786 and 9376 dating back to 1878. For the man skilled in the art the Solvay-soda process need not be further explained here. It should merely be added that mainly for economic reasons ammonia has never been replaced by TMA on a technical scale. The coupling to a chlorination process according to the present invention, however, opens up an entirely new commercial perspective.

It has further been established that if the oxychlorination, i.e. the chlorination with and the regeneration of the chlorinating liquid, is to proceed at a rate sufficiently high for practical purposes the chlorinating liquid should contain iodine as well as copper chloride or iron chloride. In the chlorination of the olefinic hydrocarbon with the chlorinating liuqid the metal loses its higher valency and iodine is reduced to iodide. Upon regeneration of the chlorinating liquid the previous state of valency is restored, i.e. copper (I) is reoxidized to copper (II), iron (II) to iron (III) and iodide to iodine, while with the amine hydrochloride as chlorine source the chloride content is restored to its proper level. In this oxydative regeneration, which is usually carried out by passing through a stream of air, oxygen or oxygen in a combination with nitrogen and/or carbon dioxide, the volatile amine is liberated and removed with the off-gas to be subsequently returned to the soda process. The process of the invention is schematically shown in the accompanying drawing. To clearly illustrate the effective coupling of the two separate processes this scheme is drawn to the combined manufacture of EDC from ethylene using copper (II) chloride and sodium bicarbonate from common salt using TMA as the volatile base. In the chlorination section C ethylene is chlorinated to EDC according to the equation:

$$C_2H_4 + 2CuCl_2 \rightarrow C_2H_4Cl_2 + 2CuCl$$

In the soda section S common salt is converted into bicarbonate by treating salt or brine with carbon dioxide in the presence of trimethyl amine:

$$NaCl + H_2O + CO_2 + (CH_3)_3N \rightarrow NaHCO_3 + (CH_3)_3N.HCl$$

Both sections are coupled by recycling their respective secondary products through section R where regeneration takes place in the presence of oxygen according to the reaction:

$$2CuCl + \tfrac{1}{2}O_2 + 2(CH_3)_3N.HCl \rightarrow 2CuCl_2 + 2(CH_3)_3N + H_2O$$

The overall result of this combined operation is that the chlorine in common salt is transferred to the hydrocarbon without its intermediate elemental separation by electrolysis, while the soda values are obtained without a chloride waste problem.

The chlorinating liquid is essentially a non-aqueous system whose liquid component is formed by a suitable solvent material. Acetonitrile and benzonitrile are possible solvents. Preferably the solvent has a boiling point above about 200° C. and as such adiponitrile has been found very useful. Further possible solvents are, for instance, to be found in the group of polyethyleneglycols, such as tetraethyleneglycol and other polyethyleneglycols having a molecular weight of up to about 600, and related compounds, such as the dimethylether of tetraethyleneglycol and butoxy ethoxy ethanol.

The concentration of the catalyst components in the chlorinating liquid is not necessarily restricted to specific limits. The composition is rather determined on the basis of the reaction conditions prevailing in the technical embodiment adopted. As a rule, however, the molar ratio of iodine to polyvalent metal should be lower than 1, whereas the molar ratio of chloride to polyvalent metal should be at least 3 and preferably above 4.

It will be evident that the process of the invention is generally applicable to the manufacture of chlorinated hydrocarbons from various olefinic substrates, including straight or branched chain aliphatic olefins having up to about 10 carbon atoms, cyclic aliphatic olefins having up to about 12 carbon atoms and alkenyl substituted aromatic compounds having from 8 to about 12 carbon atoms. Of particular interest, however, is the chlorination of ethylene to EDC which is the important starting material for the production of vinylchloride.

From a technical point of view the oxychlorination of, say, ethylene to EDC may be effected in various ways. In one commonly practised method the oxychlorination is performed substantially in one reactor adapted to receive the oxygen and chlorine source, required for the oxidative regeneration, simultaneously with the ethylene feed. A variant of this method is a batchwise alternating chlorination and regeneration.

In a second method, which is much preferred in the practice of this invention, the chlorination and regeneration are carried out separately in different reactors with a circulating chlorinating liquid. This manner of operation contributes greatly towards optimization of the two individual reactions. Thus, using the present chlorinating liquid the chlorination will generally run optimal in the range of 70° C. to 150° C. and at an effective pressure of about 100 to 1000 kPa, whereas the regeneration generally proceeds satisfactorily in the range of 20° C. to 90° C. at about 100 to 1000 kPa absolute pressure.

The optimization of the separate reactions is further enchanced by selecting the most suitable type of reactor for each step. For instance, the oxidation of the polyvalent metal and iodide proceeds rapidly enough by ensuring an intensive mixing of the air or oxygen with the spent chlorinating liquid. By maintaining the temperature at this stage relatively low, say about 30° to 60° C., the concentration of liberated amine in the off-gas will be quite low and a single washing of this gas will be sufficient. The bulk of the amine in the liquid is then recovered by stripping at a higher temperature, say up to 80° C., yielding concentrations of amine in the strip gas of up to 5% or higher. If carbon dioxide is used for stripping the amine may be recovered as a concentrated solution of the quaternary carbonic acid salt by washing the gas with water. This salt solution may then be used in the soda process while the remaining carbon dioxide is reused for stripping.

After having been regenerated the chlorinating liquid is ready for recycle to the chlorination reactor. At this point the liquid may still contain some free amine and due to slow oxidation in this medium losses of amine may be experienced in the long run. To suppress this oxidative degradation a simple neutralization with hydrogen chloride will suffice at this point. If EDC is the chlorination product the required hydrogen chloride can for example be recovered from the pyrolysis of EDC to vinylchloride.

About the operation of the amine-soda process little need to be said here as the process is known in itself and it is squarily based on the well known ammonia-soda or Solvay process as this is widely used in industry. There may be differences in degree associated with the use of the amine and the separation of its hydrochloride, instead of ammonia and ammonium chloride, but such differences are not as a rule of a fundamental nature. Normally, the sodium bicarbonate formed is further processed into soda ash by calcination and such further step is usually included by inference when one refers to a Solvay-soda process. In this respect the process of the present invention may be of added interest in that with certain amines, such as dimethyl amine, the direct formation of the soda is a distinct possibility. The invention will be further understood by reference to the following examples.

EXAMPLE I

The following is a description of a small scale closed cycle experiment.

In a 50 liter vessel linked to a vacuum line there were charged a concentrated solution of trimethylamine. HCl in water, adiponitrile and $CuCl_2.2H_2O$. The mixed charge was then heated to 90° C. under a vacuum of about 4 kPa until substantially anhydrous condition. Thereafter cuprous iodide was added to achieve a starting chlorinating liquid containing on a weight basis in adiponitrile 4,7% Cu, 5,2% I, 12,2% Cl and 20,7% TMA (molar ratio of Cl/Cu=4,7 and I/Cu=0,56). At a rate of 46 1/h the liquid was passed to an oxidation reactor consisting of three packed columns in series of 5 m length and 25,4 mm internal diameter each. Air was admitted at the bottom of the first column at a rate of 2,7 m³/h and passed cocurrently with the liquid through the columns at a temperature of 55° C. and a pressure drop from about 450 to 100 kPa. The ensueing stream was then led to the top of a packed stripper column of 5 m total length, 101,6 mm internal diameter, including two small steam heated sections. At a temperature of about 75° C. and about atmospheric pressure TMA was stripped from the liquid with carbon dioxide (flow 4 m³/h) at a rate of 6 mol/h or about 2,2 vol.-% of the exit air-carbon dioxide mixture. The oxidized and stripped chlorinating liquid was neutralized with gaseous HCl and then admixed with an ethylene flow of 7 mol/h. The mixture was first passed through a preheater to raise the temperature to 100° C. and then through a packed chlorinator column of 5 m length and 25,4 mm diameter at a pressure of 580 kPa.

After having passed with a residence time of about 30 minutes through an elongated pressure reactor consisting of a coil of 12,7 mm plastic tubing located in the above preheater the reaction mixture was admitted to a packed column of 3,8 m length and 76,2 mm internal diameter in which the EDC was removed by steam distillation. With the exit gas mixture EDC was removed at a rate of 0,56 kg EDC/h, which amounted to about 80% conversion calculated on ethylene feed. The residual spent chlorinating liquid was then returned to and dried in the initial 50 1 vessel to close the cycle on the chlorination side of the process. The TMA loaded air-carbon dioxide mixture leaving the TMA stripper mentioned above was led to the bottom of a packed column over which near saturated brine was circulated at a temperature of 15°-20° C. Since this absorption/carbonatation is well known in the art no specific attempt was made to optimize conditions nor to determine yield and conversion data in his simplified experimental set-up. Resulting sodium bicarbonate slurry was merely discharged from the column and separated by filtration. The mother liquor was concentrated by evaporation to precipitate substantially all of the remaining sodium chloride. After removing this salt by filtration the residual TMA.HCl solution of about 65% by weight strength was returned to the initial 50 1 vessel to close the cycle on the soda side of the process. The complete process described in this example was run on a continuous basis for 27 hours.

EXAMPLE II

A brief experiment was conducted to test the suitability of triethylamine (TEA) in the regeneration step. In a bubble reactor of 30 cm length and 3 cm diameter, kept at 90° C., were introduced 50 ml of adiponitrile, 0,1 mole of copper (I) chloride and 0,3 moles of TEA.HCl. The mixture was first homogenized with a nitrogen stream at a rate of 100 1/h. The nitrogen stream was then replaced with an air stream of 70 1/h and the off-gas collected in a gas absorber kept at a pH of 3 by means of an automatic titrator to determine the rate of release of TEA. This appeared to amount to 15 mmoles/h, which in principle is satisfactory.

EXAMPLE III

In a number of experiments with different solvents the suitability of dimethylamine (DMA) was tested in the bubble reactor of the previous example, maintained to 100° C. and operated with an air stream of 100 1/h. Each time the reactor was charged with 50 ml of the solvent, 50 mmole of copper (I) chloride and 200 mmoles of DMA.HCl. The theoretical quantity of DMA that can be stripped from this mixture is 50 mmoles and the percentage DMA that was released in these tests was calculated on that basis. Using the indicated solvents the following percentages were found to be released after 140 minutes of operation: 30,8% in tetraethyleneglycol, 37,4% in polyethylene glycol 600, 45% in the dimethyl ether of tetraethyleneglycol and 42,6% in butoxy ethoxy ethanol.

EXAMPLE IV

An experiment was conducted to check whether the presence of iron instead of copper also operates in the regeneration step. To this end the bubble reactor of Example II, maintained at 100° C., was charged with 50 ml of adiponitrile, 40,7 mmoles of iron (II) chloride and 270 mmoles of TMA.HCl. After homogenization an air stream of about 5 1/min was introduced and the off-gas collected in a gas absorber as in Example II. It appeared that in 80 minutes 39,9 mmoles of TMA had been released.

What is claimed is:

1. A process for the combined manufacture of chlorinated hydrocarbons and sodium bicarbonate comprising the steps of
    a. chlorinating an olefinic hydrocarbon with a substantially non-aqueous chlorinating liquid containing iodine and a chloride of a polyvalent metal in the oxidized state,
    b. converting sodium chloride by carbonatation into sodium bicarbonate with the aid of a volatile base according to the Solvay-soda method,
    c. using the hydrogen chloride adduct of the volatile base resulting from step b. as the chlorine source in the oxidative regeneration of the spent chlorinating liquid of step a.,
characterized in that the polyvalent metal in the chlorinating liquid is copper and/or iron, the volatile base in step b. is an aliphatic amine having a boiling point below about 100° C. and its hydrochloride adduct is the chlorine source in step c., the amine being recovered in the vapor phase and returned to the soda process of step b.

2. The process of claim 1, characterized in that the volatile base is trimethyl amine.

3. The process of claim 1, characterized in that the chlorinating liquid substantially contains adiponitrile as the liquid component.

4. The process of claim 1, characterized in that the chlorination with and the oxidative regeneration of the chlorinating liquid are carried out in separate reactors at temperatures respectively in the ranges of 70° to 150° C. and 20° to 90° C.

5. The process of claim 1 applied to the combined production of 1,2-dichloroethane and soda from ethylene and common salt.

* * * * *